United States Patent [19] [11] 4,199,599
Klein [45] Apr. 22, 1980

[54] GLYCERYL-TRI-3,5,5-TRIMETHYLHEXANOATE PROTECTING THE SKIN THEREWITH AND COSMETIC COMPOSITIONS THEREFORE

[75] Inventor: Erich Klein, Holzminden, Fed. Rep. of Germany

[73] Assignee: Dragoco Gerberding & Co. GmbH, Holzminden, Fed. Rep. of Germany

[21] Appl. No.: 875,090

[22] Filed: Feb. 3, 1978

[30] Foreign Application Priority Data

Jun. 27, 1977 [DE] Fed. Rep. of Germany ....... 2728922

[51] Int. Cl.$^2$ .......................... A61K 7/00; A61K 7/40; C07C 69/30
[52] U.S. Cl. ....................................... 424/311; 424/59; 424/317; 424/365; 560/263
[58] Field of Search ................ 560/263; 424/305, 307, 424/311, 317, 318, 343, 365

[56] References Cited

U.S. PATENT DOCUMENTS

| | | | |
|---|---|---|---|
| 3,329,826 | 7/1967 | Pine | 560/263 |
| 3,341,574 | 9/1967 | Taylor | 560/263 |
| 3,441,600 | 4/1969 | Chao | 560/263 |
| 4,011,251 | 3/1977 | Tjurin | 560/263 |

FOREIGN PATENT DOCUMENTS

| | | | |
|---|---|---|---|
| 664180 | 1/1952 | United Kingdom | 560/263 |
| 1031013 | 5/1966 | United Kingdom | 560/263 |

OTHER PUBLICATIONS

Matsumura, Chem Abs., vol. 79, 1973, Abs. No. 96850g.

*Primary Examiner*—Anna P. Fagelson
*Attorney, Agent, or Firm*—Browdy and Neimark

[57] ABSTRACT

Glyceryl-tri-3,5,5-trimethylhexanoate is particularly suitable for use in cosmetic preparations, particularly in skin creams used for protection against harmful outside agents.

15 Claims, No Drawings

GLYCERYL-TRI-3,5,5-TRIMETHYLHEXANOATE PROTECTING THE SKIN THEREWITH AND COSMETIC COMPOSITIONS THEREFORE

FIELD OF THE INVENTION

The present invention relates to a new compound and to new compositions of matter for cosmetic use, and more particularly to oils, creams, emulsions and ointments used as skin-protecting agents.

BACKGROUND OF THE INVENTION

Skin creams used for cosmetic purposes, which provide protection against harmful outside agents when applied to the surface of the skin, generally contain water-repellant hydrocarbons, natural or synthetic waxes, and/or natural fats.

Natural fats usually represent mixtures of the various triglycerides whose fatty acid components contain 14, 16 or 18 carbon atoms in a straight chain.

If the fatty acids are saturated, the fats usually have a firm consistency, are not stretchable, and have only slight spreadability. If the triglycerides contain unsaturated fatty acids, the solidification point drops and the fats become more stretchable or liquid, but have the disadvantage of readily turning rancid by oxidation when exposed to the air and are therefore unsuitable for cosmetic purposes. In all cases, special preservatives must be added to preparations containing natural fats.

SUMMARY OF THE INVENTION

It has now been found that glyceryl-tri-3,5,5-trimethylhexanoate, which is a new compound, is particularly suitable for use in cosmetic preparations, since the consistency and the spreadability of this branch-chained triglyceride permits it to spread well on the skin and coat it in an extremely protective manner.

The multiple branching of the carbon chain of the acid components of this triglyceride is the reason why this compound is an oily liquid at room temperature and possesses unusually great spreadability. One advantage of this compound is also that it cannot be decomposed by the bacterial flora of the skin nor changed into substances harmful to the skin because of the branching of the carbon chain which does not occur in this form in nature. Moreover, oxidation by atmospheric oxygen is impossible because of the lack of unsaturated centers and because of steric prevention of oxygen attack by the branching. This has an advantageous effect on the stability and shelf life of cosmetic products containing glyceryl-tri-3,5,5-trimethylhexanoate.

DETAILED DESCRIPTION OF PREFERRED EMBODIMENTS

When the new glycerol ester in accordance with the present invention is used in skin-protecting agents, it is usually applied in quantities of 2% to 15% according to the type of preparation.

All percent figures are in weight percent and all parts are parts by weight.

In oils, the new glycerol ester is preferably used in quantities of 5% to 15%,
in creams, in quantities of 2% to 5%,
in emulsions, in quantities of 2% to 5%, and
in ointments, in quantities of 2% to 5%.

Glyceryl-tri-3,5,5-trimethylhexanoate can be produced analogously to known process by converting glycerol with 3,5,5-trimethyl hexanoic acid chloride in the presence of a basic catalyst (B. F. Daubert and A. R. Baldwin, *J. Amer. Chem. Soc.*, Vol. 66, 1944, p. 997).

The following examples will illustrate the invention. They show the manufacture and application of the new glycerol ester.

EXAMPLE 1

Glycerol (25 g) is dissolved with pyridine (70 g) in chloroform (750 ml). 150 g 3,5,5-trimethyl hexanoic acid chloride are added slowly to this solution under agitation and this mixture is heated for two hours at 100° C. After cooling, the reaction mixture is dissolved in 3.5 liters of petroleum ether and this solution is washed first with 5% cold sulfuric acid, then with 5% sodium carbonate solution, and finally with water. The remaining organic phase is dried with sodium sulfate and the solvent is distilled off.

The glyceryl-tri-3,5,5-trimethylhexanoate yield is: 108 g (79% of theoretical); $D_4^{20}=0.9452$ $n_D^{20}=1.4482$.

EXAMPLE 2

This example shows a number of recipes for skin-protecting agents containing the new glycerol ester.

EXAMPLE 2a

| Suntan Oil | |
|---|---|
| | Parts by weight |
| Paraffin oil 5° E. | 66.0 basic-agent oil-component |
| Isopropylmyristate | 25.0 solvent |
| Glyceryl-tri-3,5,5-trimethylhexanoate | 6.0 spreading-agent |
| 5-(3,3-dimethyl-2-norbornylidene)-3-pentene-2-one | 2.0 sun-protective-agent |
| Perfume oil | 1.0 fragrance-component |
| | 100.0 |

EXAMPLE 2b

| Day Cream | |
|---|---|
| | Parts by weight |
| Glycol monostearate/sodium stearate | 12.0 emulsifier |
| Isopropylmyristate | 2.0 viscosity-agent |
| Glyceryl-tri-3,5,5-trimethylhexanoate | 2.0 spreading and care-agent |
| p-hydroxybenzoic acid ester | 0.3 preservative |
| Water | 80.4 |
| Sorbitol F | 3.0 moisture-agent |
| Perfume oil | 0.3 fragrance-component |
| | 100.0 |

EXAMPLE 2c

| Body Emulsion | |
|---|---|
| | Parts by weight |
| Glycerine monostearate | 5.0 thickening-agent |
| Silicone oil AK 350 | 0.5 oil-component |
| Isopropylmyristate | 8.0 viscosity-agent |
| Glyceryl-tri-3,5,5-trimethylhexanoate | 2.0 spreading and care-agent |
| Fat alcohol polyglycol ester | 1.0 thickening-agent |
| p-hydroxybenzoic acid ester | 0.3 preservative |
| Hydroxyalkylphosphoric acid ester | 3.5 emulsifier |
| Propylene glycol | 3.0 moisture-agent |
| Glycerol | 2.0 moisture-agent |
| Water | 74.3 |

-continued

| Body Emulsion | |
|---|---|
| | Parts by weight |
| Perfume oil | 0.4 fragrance-component |
| | 100.0 |

EXAMPLE 2d

| Oil Bath | |
|---|---|
| | Parts by weight |
| Fat alcohol polyglycol ether | 15.0 solvent |
| Glyceryl-tri-3,5,5-trimethylhexanoate | 15.0 spreading-agent |
| Isopropylmyristate | 20.0 solvent |
| Paraffin oil 5° E. | 45.0 basic-agent |
| Perfume oil | 5.0 fragrance-component |
| | 100.0 |

EXAMPLE 2e

| Skin Ointment | |
|---|---|
| | Parts by weight |
| Solid paraffin | 4.4 thickening-agent |
| Anhydrous lanolin | 4.4 Lubrication-agent |
| Sorbitansesquioleate | 2.6 emulsifier |
| Palmitic acid cetylic ester | 2.2 thickening-agent |
| Lanolin alcohol | 1.8 emulsifier |
| Oleic acid decyl ester | 5.7 oily-compound |
| 1-hydroxystearine | 0.9 thickening-agent |
| Butylhydroxytoluene | 0.1 antioxidant |
| Isopropylmyristate | 3.0 viscosity-agent |
| Glyceryl-tri-3,5,5-trimethylhexanoate | 3.0 spreading and care-agent |
| p-hydroxybenzoic acid ester | 0.3 preservative |
| Magnesium sulfate | 0.5 stabiliser |
| 1,2-propylene glycol | 3.0 moisture-agent |
| Water | 67.6 |
| Perfume oil | 0.5 fragrance-component |
| | 100.0 |

The novel glyceryl-tri-3,5,5-trimethylhexanoate may also be added to base compositions for any preparations which are to be applied to the skin, to which base compositions in a further step of manufacture are then added further compounds as for instance perfume oils and/or pharmaceutically active agents and other usual components to make the final product.

Such base compositions are for instance:

| A. for Suntan Oil: | Light protection agents in oil base |
|---|---|
| B. for Day Creams, Body Emulsions and Skin Ointments: | Fatty and water bearing component and emulsifiers (for controlling fat and water balance of the skin) |
| C. for Oil Bath: | Oil component as base. |

Such base compositions are often supplied to manufacturers of medical or cosmetic creams or other preparations for use on the skin by other manufacturers who are specialized in such base compositions but do not produce the final preparation. The novel spreading agent glyceryl-tri-3,5,5-trimethylhexanoate may be incorporated into the base composition as there is no danger of deterioration during storage due to its inert chemical nature which also provides for good compatibility with practically all perfumes, flavoring agents and pharmaceutically active substances used for application on the skin.

The novel spreading agent enhances spreading of preparations containing it. Not only does a given amount of the preparation spread wider but spreading is also faster and it is possible to get thinner but still coherent films from a given amount of the preparation than with known spreading agents used in such preparations.

If the novel spreading agent is added to base compositions the addition is done in such an amount that the final preparation contains the amounts shown earlier in this connection for the final preparations i.e. oils, creams, emulsions and ointments.

It will be obvious to those skilled in the art that various changes may be made without departing from the scope of the invention and the invention is not to be considered limited to what is shown in the drawings and described in the specification.

What is claimed is:

1. Glyceryl-tri-3,5,5-trimethylhexanoate.

2. A cosmetic composition which provides protection for the skin against harmful outside agents comprising 2–15% by weight of the compound of claim 1 and cosmetic adjuvants.

3. A composition in accordance with claim 2 wherein said composition is an oil and said compound is present in the amount of 5–15% by weight.

4. A composition in accordance with claim 2 wherein said composition is a cream and said compound is present in the amount of 2–5% by weight.

5. A composition in accordance with claim 2 wherein said composition is an emulsion and said compound is present in the amount of 2–5% by weight.

6. A composition in accordance with claim 2 wherein said composition is an ointment and said compound is present in the amount of 2–5% by weight.

7. A method of protecting the skin comprising applying the composition of claim 2 in an amount sufficient therefor.

8. A cosmetic composition for protecting the skin, having an enhanced spreadability comprising a skin protecting amount of a skin protecting agent and cosmetic adjuvants, wherein at least a portion of said skin protecting agent comprises a spreadability enhancing amount of the compound of claim 1.

9. A composition in accordance with claim 8 wherein said preparation is an oil, cream, emulsion or ointment.

10. A composition in accordance with claim 8 wherein said composition is an oil and said spreadability enhancing amount of said compound is 5–15% by weight.

11. A composition in accordance with claim 8 wherein said composition is a cream and said spreadability enhancing amount of said compound is 2–5% by weight.

12. A composition in accordance with claim 8 wherein said composition is an emulsion and said spreadability enhancing amount of said compound is 2–5% by weight.

13. A composition in accordance with claim 8 wherein said composition is an ointment and said spreadability enhancing amount of said compound is 2–5% by weight.

14. A composition in accordance with claim 8 wherein all of said skin protecting agent is said compound.

15. A method of protecting the skin comprising applying the composition of claim 8 in an amount sufficient therefor.

* * * * *